United States Patent [19]

Kohama et al.

[11] Patent Number: 5,185,262

[45] Date of Patent: Feb. 9, 1993

[54] DNA FRAGMENT CONTAINING GENE WHICH ENCODES THE FUNCTION OF STABILIZING PLASMID IN HOST MICROORGANISM

[75] Inventors: Keiko Kohama; Miki Kobayashi; Yasurou Kurusu; Hideaki Yukawa; Makiko Fukushima, all of Ami, Japan

[73] Assignee: Mitsubishi Petrochemical Co., Ltd., Tokyo, Japan

[21] Appl. No.: 473,396

[22] Filed: Feb. 1, 1990

Related U.S. Application Data

[63] Continuation-in-part of Ser. No. 385,414, Jul. 26, 1989, abandoned.

[30] Foreign Application Priority Data

| | | | |
|---|---|---|---|
| Jul. 27, 1988 | [JP] | Japan | 63-185428 |
| Sep. 8, 1988 | [JP] | Japan | 63-223399 |
| Jan. 19, 1989 | [JP] | Japan | 1-8577 |
| Jan. 25, 1989 | [JP] | Japan | 63-14098 |

[51] Int. Cl.$^5$ .............................. C12N 15/77
[52] U.S. Cl. .................. 435/320.1; 536/24.1; 435/252.32
[58] Field of Search ............ 536/27; 435/172.3, 320.1, 435/91, 252.3

[56] References Cited

U.S. PATENT DOCUMENTS

| | | | |
|---|---|---|---|
| 4,520,103 | 5/1985 | Ensley et al. | 435/121 |
| 4,649,119 | 3/1987 | Sinskey et al. | 435/317.1 |
| 4,760,022 | 7/1988 | Molin et al. | 435/320.1 |
| 4,885,245 | 12/1989 | Ishida et al. | 435/172.3 |
| 4,980,285 | 12/1990 | Sana et al. | 435/172.3 |

FOREIGN PATENT DOCUMENTS

| | | | |
|---|---|---|---|
| 0136359 | 4/1985 | European Pat. Off. | 435/172.3 |
| 0169377 | 1/1986 | European Pat. Off. | 435/172.3 |
| 0183175 | 6/1986 | European Pat. Off. | 435/172.3 |
| 63-27971 | 11/1988 | Japan | 435/320.1 |

OTHER PUBLICATIONS

Smith et al. (1986), Appl. Environ., Micro, vol. 51, pp. 634–639.
Santamaria et al. (1987), Gene, vol. 56, pp. 199–208.
Patek et al. (1989), Appl. Microbiol. Biotech., vol. 31, pp. 65–69.

*Primary Examiner*—Richard A. Schwartz
*Assistant Examiner*—James Ketter
*Attorney, Agent, or Firm*—Wenderoth, Lind & Ponack

[57] ABSTRACT

A DNA fragment derived from plasmid pBY503 obtained from *Brevibacterium stationis* IFO12144, said DNA fragment containing a gene which encodes for the function of maintaining a plasmid, capable of replicating and proliferating at least in a Coryneform bacteria of the genus Brevibacterium, stably in said bacteria; and a vector DNA capable of replicating and proliferating in a Coryneform bacteria into which the above DNA fragment is introduced.

11 Claims, 1 Drawing Sheet

DNA FRAGMENT CONTAINING GENE WHICH ENCODES THE FUNCTION OF STABILIZING PLASMID IN HOST MICROORGANISM

This application is a continuation-in-part application of Ser. No. 07/385,414 of Jul. 26, 1989, now abandoned.

BACKGROUND OF THE INVENTION

This invention relates to a DNA fragment containing a gene which encodes the function of stabilizing a plasmid in a host microorganism. More specifically, it relates to a DNA fragment which contains a gene encoding a stabilizing function, and is derived from plasmid pBY503 obtained from *Brevibacterium stationis* IFO12144, and to its use.

Coryneform bacteria including bacteria of the genus Brevibacterium are industrially useful microorganisms which produce amino acids, organic acids and purine nucleotide. The molecular breeding of Coryneform bacterial strains by the introduction of the recombinant DNA technology is still behind that of *Escherichia coli* strains. Particularly, it is strongly desired to develop industrially useful vectors of excellent stability using Coryneform bacteria as hosts.

Generally, with regard to the stability of constructed plasmids in hosts, various cases of genetic instability, such as segregating of a plasmid from a host during cultivation or deletion of an inserted gene, have been reported, and countermeasures against it have been considered.

For example, there was proposed a method of stabilizing the properties of a microorganism containing a plasmid, in which a plasmid having inserted thereinto a chromosomal gene DNA fragment coding for the property of not depending upon streptomycin derived from *Escherichia coli* is included in a streptomycin-dependent mutant of the genus Escherichia (Japanese Laid-Open Patent Publication No. 156591/1980). This method, however, is economically disadvantageous. Furthermore, since it is necessary to insert complex functions into the plasmid, it is foreseen that the plasmid will have difficulty in being distributed stably to daughter cells at the time of fission and proliferation of the host. Accordingly, it would encounter various problems before it could be successfully applied industrially.

Most of commercially useful natural plasmids obtained from Coryneform bacteria including bacteria of the genus Brevibacterium do not have a drug-resistant gene which can be a plasmid marker and are devoid of cloning sites to which useful genes can be bound. Accordingly, although these natural plasmids have a possibility of genetically improving bacteria of this genus, they are unsuitable for molecular breeding of Coryneform bacteria.

The present inventors previously developed industrially useful plasmid vectors such as pCRY2 and pCRY3 by introducing a drug-resistant marker, cloning sites, and a gene region necessary for replication in *Escherichia coli* into natural plasmid pBY502 or pBY503 (see Japanese Laid-Open Patent Publication No. 191686/1989). However, these plasmid vectors show considerable instability in bacterial cells and are not fully efficient in producing gene products in large quantities within the cells.

It is desired therefore to develop a method of stabilizing a plasmid, in which the plasmid is accurately distributed through generations from parent cells to daughter cells within cells of a transformed microorganism.

SUMMARY OF THE INVENTION

As a result of extensive investigations, the present inventors found that a gene which encodes for the function of maintaining a plasmid, capable of replicating and proliferating at least in a Coryneform bacteria of the genus Brevibacterium, stably in the above bacterium, exists on pBY503 derived from *Brevibacterium stationis* IFO12144 which can replicate and proliferate within a Coryneform bacteria. For convenience, this gene is sometimes referred to herein as the "stabilizing gene", and the above function, as the "stabilizing function".

The present inventors have now succeeded in isolating a DNA fragment containing this stabilizing gene from pBY503.

Thus, according to this invention, there is provided a DNA fragment derived from plasmid pBY503 obtained from *Brevibacterium stationis* IFO12144, said DNA fragment containing a gene which codes for the function of maintaining a plasmid, capable of replicating and proliferating at least in a Coryneform bacteria of the genus Brevibacterium, stably in said bacterium.

By using the DNA fragment of the invention, a vector DNA which can stably replicate and proliferate in bacteria of the genus Brevibacterium or other Coryneform bacteria can be constructed. Industrially useful Coryneform bacteria can be bred by introducing a useful structural gene into this vector DNA and transforming Coryneform bacteria with it.

DETAILED DESCRIPTION OF THE PREFERRED EMBODIMENTS

The DNA fragment of this invention will be described below in detail.

Figure 1:
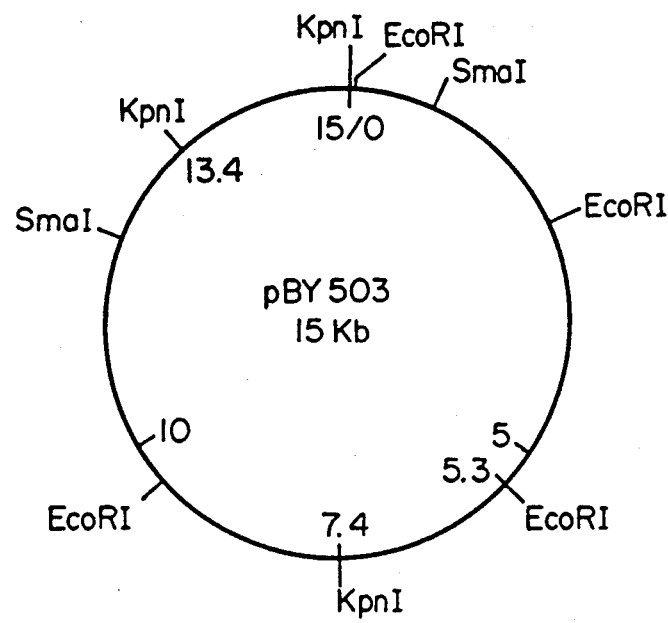
FIG. 1 shows the cleavage map of plasmid pBY503 with restriction endonucleases KpnI, EcoRI and SmaI.

The DNA fragment of this invention containing the stabilizing gene (this DNA fragment will be referred to as the "stabilized DNA fragment") exists on plasmid pBY503 (size about 15 kb; see FIG. 1; see also Japanese Laid-Open Patent Publication No. 95785/1989) obtained from *Brevibacterium stationis* IFO12144 [deposited Jul. 18, 1988 at the Fermentation Research Institute, Agency of Industrial Science and Technology, Japan, 1-3, Higashi 1-chome Tsukuba-shi, Ibaraki-ken, 305, Japan, under FERM P-10136 (transferred to international deposition under FERM BP-2515 on Jul. 12, 1989 under the Budapest Treaty)], and can be obtained by the following method from a fragment resulting from digestion of plasmid pBY503 with a suitable restriction endonuclease.

Specifically, plasmid pBY503 containing the stabilized DNA fragment is digested with a suitable restriction endonuclease. The resulting DNA fragment is inserted into a vector plasmid which is unstable in Coryneform bacteria and holds a drug-resistant marker. The vector plasmid is then introduced into a Coryneform bacteria by transformation through an electroporation method.

A plasmid DNA is extracted from the transformant and analyzed by using restriction endonucleases to examine the inserted DNA fragment derived from pBY503.

Strains containing the recombinant plasmid are cultivated under a non-selective pressure through several tens of generations. Cells which hold the plasmid at a higher rate after cultivation than the original vector plasmid are separated as recombinant plasmids containing the stabilized DNA fragment.

Figure 2:
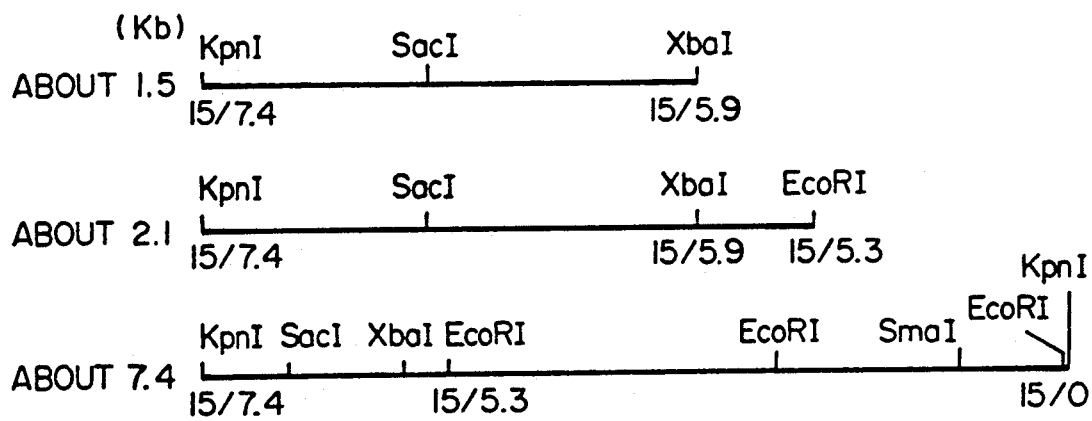
FIG. 2 shows the cleavage map of the stabilized DNA fragment with restriction endonucleases KpnI, SacI, XbaI, EcoRI and SmaI.

One stabilized DNA fragment so obtained is a DNA fragment having a size of about 7.4 kb obtained by digesting the plasmid pBY503 with restriction endonuclease Kpn I. See FIG. 2.

Table 1 shows the number of recognition sites and the size of the fragments when this stabilized DNA fragment having a size of about 7.4 kb is digested with various restriction endonucleases.

In the present invention, the "number of recognition sites" by a restriction endonuclease can be determined from the number of separable fragments which is examined by completely digesting the DNA fragment or plasmid with an excess of a restriction endonuclease and subjecting the digestion product to agarose gel electrophoresis and polyacrylamide gel electrophoresis.

The "size of a fragment" and the sizes of the individual DNA fragments of a plasmid are calculated on the basis of a standard line drawn by migration distances on the same agarose gel of a DNA fragment of a known molecular size obtained by digesting DNA of $\phi \times 174$ phage of Escherichia coli with restriction endonuclease Hind III when agarose gel electrophoresis is used; and on the basis of a standard line drawn by migration distances on the same polyacrylamide gel of a DNA fragment of a known molecular size obtained by digesting DNA of $\phi \times 174$ phage of Escherichia coli with restriction endonuclease Hae III. The size of the plasmid is calculated by adding the sizes of the individual fragments. In the determination of the sizes of the individual DNA fragments, fragments of at least 1 kb is determined by using the results obtained by 1 % agarose gel electrophoresis, and fragments of about 0.1 kb to less than 1 kb, by using the results obtained by 4 % polyacrylamide gel electrophoresis.

TABLE 1

| Restriction endonucleases | Number of recognition sites | Size (kb) of the fragment |
| --- | --- | --- |
| EcoR I | 3 | 2.7, 2.5, 2.1, 0.1 |
| Xba I | 1 | 5.9, 1.5 |
| Sac I | 1 | 6.8, 0.6 |
| Sma I | 1 | 6.4, 1.0 |

It has been confirmed that in Table 1, the 6.8 kb SacI-KpnI fragment, 6.4 KpnI-SmaI fragment, 2.1 kb KpnI-EcoRI fragment and 1.5 KpnI-XbaI fragment also have the stabilizing function. Accordingly, these fragments are included within the stabilized DNA fragment of the invention.

The stabilized genes are considered to be contained in the about 2.1 kb DNA fragment obtained by digesting plasmid pBY503 with restriction endonucleases Kpn I and EcoR I, and the about 1.5 kb DNA fragment obtained by digesting the above plasmid with Kpn I and Xba I. See FIG. 2.

The about 2.1 kb DNA fragment is digested with various restriction endonucleases, and the number of recognition sites and the sizes of the fragments obtained are shown in Table 2.

TABLE 2

| Restriction endonucleases | Number of recognition sites | Size (kb) of the fragment |
| --- | --- | --- |
| Sac I | 1 | 1.4, 0.7 |
| Xba I | 1 | 1.8, 0.3 |
| Hind III | 1 | 1.6, 0.5 |
| Kpn I | 0 | 2.1 |

By digesting plasmid pBY503 with Kpn I and Xba I, a DNA fragment having a size of about 1.5 kb can be obtained. Its nucleotide sequence can be determined by the dideoxy chain termination method [see F. Sanger et al.: Proc. Natl. Acad. Sci., U.S.A. 74, 5463 (1977)] by using plasmid pUC18 or pUC19 [see J. Messing and J. Vieira: Gene, 19, 269 (1982)]. The nucleotide sequence so determined of the DNA fragment having a size of about 1.5 kb consists of 1763 base pairs as shown below.

| 10 | 20 | 30 | 40 | 50 | 60 |
| --- | --- | --- | --- | --- | --- |
| GGTACCCGTA | TTTATGGTTA | AGGAGTGAGA | ATGATTCTAG | GAATCGTTAA | CATTAAGGC |
| 70 | 80 | 90 | 100 | 110 | 120 |
| GGGGTGGGAA | AAACAACGAC | GGCAATCTTA | TCTCGGTAGC | GCTCTTGCTG | CTGAAGGTAA |
| 130 | 140 | 150 | 160 | 170 | 180 |
| AAAGGTCACG | CTGATAGATC | TTGACCGTCA | AGGCACTGCG | ATGGATTGGG | CGGAATCCGC |
| 190 | 200 | 210 | 220 | 230 | 240 |
| TGAAGAAGCT | GGCACGCCAT | TGGACTTTGA | AGTCTCGATA | GCTATTCCTC | GACAGCTCGA |
| 250 | 260 | 270 | 280 | 290 | 300 |
| GCGCATTACC | TCCTTGCTAG | CTGATGATGA | GGTAGTCATC | ATTGATACAC | CGCCTGGAGA |
| 310 | 320 | 330 | 340 | 350 | 360 |
| CGAACCAATC | TATCAACGCC | ACGTTGCAGG | TATCGGATTT | CATTATCATC | CCTGCCGCCC |
| 370 | 380 | 390 | 400 | 410 | 420 |
| CGCAGCGCGA | ATGTGGCGCA | GATGTGGAAA | GTTATCGACG | TTCTTGAGCA | AACCCCTTAT |
| 430 | 440 | 450 | 460 | 470 | 480 |
| GCTGCTTTGC | TTACTCAAGT | GCGTGCTGGA | ACGACCGCAA | TATCGGAAGC | AGTCGATGCG |
| 490 | 500 | 510 | 520 | 530 | 540 |
| CTTAAACAGG | CGGATGTGAG | TTTCTTTGAA | ACGTTATTCC | TTGCGAGAGG | CTTTTCACCG |
| 550 | 560 | 570 | 580 | 590 | 600 |
| CAGTTTCAGG | ACTAAACCAA | CTGATTTAGG | TGAGTACACC | CAGGTTCTCG | CCGAGATAAA |
| 610 | 620 | 630 | 640 | 650 | 660 |
| GGAGTCGTTT | TAATGGCCGT | TCAAAAGACC | AATTCTATGA | AGCGCCAGCC | TAAATCCACC |
| 670 | 680 | 690 | 700 | 710 | 720 |
| GCACGAGAGT | CAGCGGATAT | TCGAAAGCCT | TTGCCTCACG | CAATCAAAGC | GATCATACTG |
| 730 | 740 | 750 | 760 | 770 | 780 |
| TCAAGCTCAC | CGTGGAGCTT | GATTCACGTC | TTCACCGTTG | AGCTCACAAG | TGCCGCAGCT |
| 790 | 800 | 810 | 820 | 830 | 840 |

| | | | | | |
|---|---|---|---|---|---|
| TTGCAGTCTG 850 | TGACCATGCG 860 | AGAGATTATT 870 | CACGACGCCG 880 | TAGAAGCAGA 890 | GCTAAAAAAG 900 |
| CATAAGAACT 910 | AGCTGCTGTA 920 | TTTACGGGTA 930 | CTGTATTTAC 940 | AGCTATACAG 950 | TTCCCCGTTC 960 |
| ATTGGCGTTA 970 | TTTCACCCGC 980 | CGCGAGCATC 990 | GTTTACTGAA 1000 | TTAGCTCAGA 1010 | GGCCAACGCT 1020 |
| TCATAATCTG 1030 | GCATATCATC 1040 | GGGAATACGG 1050 | CAGCACTGAG 1060 | CATCCTCGCT 1070 | ATAACCTATG 1080 |
| GCAGCGCTCT 1090 | TGCGGGTCGC 1100 | TTTAACGCCT 1110 | ACCTTGTTCA 1120 | ACATTTCTTG 1130 | ATACATAGGT 1140 |
| TCATCCGTTC 1150 | TCGGCCACAG 1160 | CCAAACATGA 1170 | TGGTCGGCGC 1180 | ATTGATAGCC 1190 | AAAAGGGTCC 1200 |
| GACGTGTTGG 1210 | TTCAACAGAC 1220 | ATCGACGAGC 1230 | CATCGAAGGG 1240 | TACTACACAG 1250 | TCGACGATGA 1260 |
| CGACTGCATC 1270 | ATCGCCAAGA 1280 | GATACCTCAA 1290 | GCTGTTGAAT 1300 | ATTGGCGCGA 1310 | AGTCGTGCCA 1320 |
| AGCTCAGCTA 1330 | TCTCATGAGC 1340 | TTGTAGCATT 1350 | GCATCAATCG 1360 | GAAACTCGTG 1370 | AACCTCAATG 1380 |
| GGGCTGACAT 1390 | TGCCGTTTTG 1400 | ATGTGCAAGC 1410 | TTGAGCCAGT 1420 | GTGCTGCCCC 1430 | TCCGTCCATG 1440 |
| AGGTGTCTGC 1450 | GATGCGACGT 1460 | TTTTTGCCCC 1470 | TCCGGCTATA 1480 | CGCTTCTGCC 1490 | AATAGCGCGG 1500 |
| CGTTGGTGCT 1510 | GCGCATGAGG 1520 | CCGCCTTTAA 1530 | GGTTTGCTAC 1540 | TGAGATAATC 1550 | ATGTCTGCCT 1560 |
| TCCCGTGCGT 1570 | TGTGGATTCC 1580 | CCAAAATGAT 1590 | ACTTATAGTC 1600 | TGTCGACCTA 1610 | AGGGTTCACC 1620 |
| GCTCGATTCT 1630 | GGATAGGTGG 1640 | TTGAAGATCA 1650 | GCGCCTATTG 1660 | CAGGAAGTAG 1670 | GCAACGAGTC 1680 |
| CGGTCTGCAC 1690 | GTAAAGAAAA 1700 | GGGATTGTCG 1710 | CAAGAAAGTC 1720 | TTGCTCATCT 1730 | TTCAGGACTG 1740 |
| CACCGACATA 1750 | CGTCAGCTCG 1760 | ATTGAGCGCG | GGGAGCGGAA | TCTCTCAGTG | CTTAATTTGC |
| TTACCCTGGC | AACTAGTTCT | AGA | | | |

It has not yet been determined accurately what portion of this nucleotide sequence bears the stabilized gene. It is presumed to be contained in the latter half of this nucleotide sequence.

The stabilized DNA fragment having the above nucleotide sequence may include not only one isolated from a natural plasmid, but also one synthesized by an ordinary DNA synthesizer, such as System-1 Plus supplied by Beckmann Co.

So long as the stabilizing function is not substantially impaired in the stabilized DNA fragment of the invention obtained from plasmid pBY503, some bases in the above nucleotide sequence may be substituted or deleted, or new bases may be inserted. Alternatively, some of the bases in the nucleotide sequence may be relocated. All of such derivatives are to be construed to be embraced within the stabilized DNA fragment of the present invention.

By introducing the stabilized DNA fragment of this invention into a DNA fragment or a plasmid containing a gene which encodes the function of replicating and proliferating function within Coryneform bacteria, a vector DNA having excellent stability in Coryneform bacteria can be produced.

Examples of plasmid vectors containing the genes which encode the function of replicating and proliferating in Coryneform bacteria into which the stabilized DNA fragments of the invention can be inserted include plasmids pCRY2 and pCRY3 disclosed in Japanese Laid-Open Patent Publication No. 191686/1989, pAM330 described in Japanese Laid-Open Patent Publication No. 67679/1983, plasmid pHM1519 described in Japanese Laid-Open Patent Publication No. 77895/1983, plasmids pAJ655, pAJ611 and pAJ1844 described in Japanese Laid-Open Patent Publication No. 192900/1982, plasmid pCG1 described in Japanese Laid-Open Patent Publication No. 134500/1982, plasmid pCG2 described in Japanese Laid-Open Patent Publication No. 35197/1983, and plasmids pCG4 and pCG11 described in Japanese Laid-Open Patent Publication No. 183799/1982. Preferred are plasmids used in a host-vector system for Coryneform bacteria of the genus Brevibacterium, for example pAM330, pHM1519, pCG1, pCG4, pBY502 and pBY503, especially those containing a gene encoding the function of replicating and proliferation and derived from pBY502 and pBY503. For example, the plasmids pCRY2 and pCRY3 are favorably used.

The above plasmid vectors pCRY2 and pCRY3 may be constructed as follows. To construct pCRY2, plasmid pBY502 DNA from *Brevibacterium flavum* MJ233 (FERM BP-1497) is digested with restriction endonuclease Hind III to obtain a DNA fragment having a size of 4.1 kb and then this DNA fragment ligated with the same restriction endonuclease digested pHSG398 (see S. Takeshita et al., *Gene*, 61 (1987) pp. 63–74; a product of Takara Shuzo Co., Ltd.). To construct pCRY3, plasmid pBY503 from *Brevibacterium stationis* IFO12144 (FERM BP-2515) is digested with restriction endonuclease Kpn I to obtain a DNA fragment having a size of 6 kb and then this DNA fragment is ligated with the plasmid pHSG398 (a method of Takara Shuzo Co., Ltd.) digested by the same restriction endonuclease (see the specification of Japanese Laid-Open Patent Publication No. 191686/1989). By cutting out a DNA fragment containing a gene which encodes the function of replication and proliferation within Coryneform bacteria from the aforesaid plasmid vectors, and ligating it with the stabilized DNA fragment of this invention, a vector DNA can be obtained which has excellent stability within Coryneform bacteria and can replicate and proliferate.

Introduction of the stabilized DNA fragment of the invention into the above plasmid vector (e.g., pCRY2 or pCRY3) may be effected, for example, by digesting the plasmid vector pCRY2 or pCRY3 completely or partially with restriction endonuclease Kpn I, or both Kpn I and EcoR I, or both Kpn I and Xba I, and ligating the digestion product with the stabilized DNA fragment of the invention (having a size of about 7.4 kb, about 2.1 kb or 1763 bp).

DNA fragments containing structural genes encoding various industrially useful substances may be inserted into the vector DNA so treated which contains the stabilized gene and can replicate and proliferate in Coryneform bacteria. By introducing such a vector DNA having inserted thereinto a useful gene into a host microorganism and cultivating the host microorganism, the useful substance encoded by the useful gene can be produced stably and efficiently.

Examples of the DNA containing useful structural genes which can be inserted into the vector DNA in accordance with this invention include a DNA fragment at least containing trp B and trp A [tryptophan synthase (EC 4.2.1.20)] genes or a tna A [tryptophanase (EC 4.1.99.1)] gene and a promoter and an operator capable of controlling the expression of the above genes; a gene encoding tyrosine phenol-lyase (EC 4.1.99.2); a gene encoding threonine biosynthesizing enzymes [such as aspartate kinase (EC 2.7.2.4), homoserine dehydrogenase (EC 1.1.1.3), homoserine kinase (EC 2.7.1.39) and threonine synthase (EC 4.2.99.2)]; and a gene encoding isoleusine biosynthesizing enzymes [such as threonine deaminase (EC 4.2.1.16), acetohydroxyacid synthase (EC 4.1.3.18), acetohydroxyacid isomeroreductase (EC 1.1.1.86), dihydroxyacid dehydrase (EC 4.2.1.9) and transaminase (EC 2.6.1.42), etc.

Examples of the host microorganism which can be transformed by the vector DNA having inserted thereinto the useful gene include Coryneform bacteria such as *Brevibacterium flavum* MJ233 (FERM BP-1497), *Brevibacterium flavum* MJ233-AB-41 (FERM BP-1498), *Brevibacterium flavum* MJ233-ABT-11 (FERM BP-1500), and *Brevibacterium flavum* MJ233-ABD-21 (FERM BP-1499).

The strain FERM BP-1498 is an ethanol-assimilating microorganism to which DL-α-aminobutyric acid resistance is positively imparted using the strain FERM BP-1497 as a parent (see Japanese Patent Publication No. 28398/1984, columns 3-4). The strain FERM BP-1500 is a highly L-α-aminobutyric acid transaminase active mutant of the strain FERM BP-1497 as a parent. The strain FERM BP-1499 is a highly D-α-aminobutyric acid deaminase active mutant of the strain FERM BP-1497 as a parent (see Japanese Laid-Open Patent Publication No. 177993/1986).

Other host microorganims that can be used include, for example, *Brevibacterium ammoniagenes* ATCC6871, ATCC13745 and ATCC13746, *Brevibacterium divaricatum* ATCC14020, *Brevibacterium lactofermentum* ATCC13869 and *Corynebacterium glutamicum* ATCC31830.

Among these microorganisms described above, *Brevibacterium flavum* MJ-233 (FERM BP-1497), *Brevibacterium flavum* MJ-233-AB-41 (FERM BP-1498), *Brevibacterium flavum* MJ-233-ABD-21 and *Brevibacterium flavum* MJ-233-ABT-11 have been deposited under deposit numbers FERM BP-1497, FERM BP-1498, FERM BP-1499 and FERM BP-1500, respectively, at Fermentation Research Institute, Agency of Industrial Science and Technology, 1-3, Higashi 1-chome, Tsukuba-shi, Ibaraki-ken 305, Japan under the Budapest Treaty. *Brevibacterium ammoniagenes* (ATCC6871, ATCC13745 and ATCC13746), *Brevibacterium divaricatum* (ATCC14020), *Brevibacterium lactofermentum* (ATCC13869) and *Corynebacterium glutamicum* (ATCC31830) are microorganisms described in American Type Culture Collection, Catalogue of Bacteria and phages.

When *Brevibacterium flavum* MJ233 is used, it sometimes become difficult to transform it owing the to plasmid pBY502 it contains (see Japanese Laid-Open Patent Publication No. 36787/1988). In such a case, it is desirable to remove plasmid pBY502 from this microorganism. This plasmid can be caused to drop out naturally by repeated subcultivation, for example, or it can be artificially removed, for example, by the method described in Bact. Rev., 36, 361-405 (1972).

One example of artificially removing the plasmid is specifically shown below. *Brevibacterium flavum* MJ233 is inoculated at a rate of about 10 cells in a medium containing Acridine Orange (concentration: 0.2 to 50 μg/ml) or ethidium bromide (concentration 0.2 to 50 μg/ml) in concentrations which incompletely inhibit the growth of the above microorganism, and cultivated at 35° C. for about 24 hours while inhibiting its growth incompletely. The culture broth is diluted and then spread on an agar plate, and cultivated at 35° C. for about 2 days. The plasmid extracting operation was carried out on the resulting clones independently from each other. Strains from which the plasmid has been removed are selected. By this procedure, *Brevibacterium flavum* MJ233 from which pBY502 has been removed is obtained.

The transformation of the above host organisms with the recombinant DNA may be carried out by known methods, for example the electroporation method described in the literature, such as Calvin, N. M. and Hanawalt, P. C., Journal of Bacteriology, 170, 2796 (1988), and Tao, K., Nishida, T. and Izaki, K., Agricultural and Biological Chemistry, 62, 293 (1988). For example, it can be effected by passing a current of pulse waves through the host microorganism.

The following examples illustrate the present invention more specifically. It should be understood that these examples are given as an aid to a specific recognition of the present invention, and do not limit the scope of the invention in any way.

EXAMPLE 1

Construction of Plasmid pCRY2 Composed of Plasmid pBY502 and Plasmid pHSG398, and Its Properties A) Preparation of Plasmid pBY502

Plasmid pBY502 is a plasmid having a molecular size of about 30 megadaltons (about 45 kb) newly isolated from *Brevibacterium flavum* MJ233 (FERM BP-1497) and is described in Japanese Laid-Open Patent Publication No. 36787/1988. The plasmid pBY502 was prepared by the following method.

*Brevibacterium flavum* MJ233 (FERM BP-1497) was cultivated till the later stage of the logarithmic growth period in 1 liter of a semi-synthetic medium (medium A) [composition: 2 g of urea, 7 g of $(NH_4)_2SO_4$, 0.5 g of $K_2HPO_4$, 0.5 g of $KH_2PO_4$, 0.5 g of $MgSO_4$, 6 mg of $FeSO_4 \cdot 7H_2O$, 6 mg of $MnSO_4 \cdot 4$–$6H_2O$, 2.5 g of yeast extract, 5 g of Casamino acid, 200 μg of biotin, 200 μg of thiamine hydrochloride, 20 g of glucose and 1 liter of deionized water]. The cells were harvested and suspended in 20 ml of a buffer (containing lysozyme in a concentration of 10 mg/ml 25 mM tris(hydroxymethyl)aminomethane, 10 mM EDTA, 50 mM glucose], and incubated at 37° C. for 1 hour. To the reaction solution was added 40 ml of alkaline-SDS solution [0.2N NaOH, 1% (w/v) SDS]. They were gently mixed and left to stand at room temperature for 15 minutes.

Then, 30 ml of a potassium acetate solution [60 ml of a 5 M potassium acetate solution, 11.5 ml of acetic acid, and 28.5 ml of deionized water] was added to the reaction solution. They were fully mixed, and then were chilled for 15 minutes by ice water.

All the lyzate was transferred to a centrifugal tube, and centrifuged at 4° C. for 10 minutes at 15,000×G.

To the supernatant was added an equal amount of a phenol/chloroform solution (1:1). The mixture was suspended, and then transferred to a centrifugal tube, and then centrifuged at room temperature for 5 minutes at 15,000×G. The aqueous layer was recovered. Ethanol in a two-fold amount was added to the aqueous layer, and the mixture was allowed to stand at −20° C. for 1 hour. It was centrifuged at 4° C. for 10 minutes at 15,000×G. The precipitate was recovered. The precipitate was dried under reduced pressure and dissolved in 2 ml of a TE buffer [10 mM Tris, 1 mM EDTA; adjusted to pH 8.0 with HCl]. To the solution were added 15 ml of a cesium chloride solution [prepared by dissolving 170 g of cesium chloride to 100 ml of a TE buffer in a 5-fold concentration] and 1 ml of an ethidium bromide solution (10 mg/ml) to adjust the density to 1.392 g/ml. This solution was centrifuged at 12° C. for 42 hours at 116,000×G.

Plasmid pBY502 was detected as a lower band in the centrifugal tube by ultraviolet irradiation. By pulling out this band from the side surface of the centrifugal tube by an injection syringe, a fraction containing plasmid pBY502 was obtained.

Then, this fraction was treated four times with an equivalent of isoamyl alcohol to extract and remove ethidium bromide and then dialyzed against TE buffer. To the resulting dialyzate containing plasmid pBY502 was added a 3 M sodium acetate solution so that its final concentration became 300 mM. Ethanol in a two-fold amount was added, and the mixture was left to stand at −20° C. for 1 hour. The solution was centrifuged at 15,000×G to precipitate the DNA and about 20 μg of plasmid pBY502 was obtained.

B) Preparation of Plasmid pHSG398

Plasmid pHSG398 replicates in *Escherichia coli*, has a molecular size of about 1.4 megadaltons, and is resistant to chloramphenicol. It is commercially available and can be purchased from Takara Shuzo Co., Ltd.

C) Construction of Plasmid pCRY2

Plasmid pHSG398 (0.5 μg) was digested completely with restriction endonuclease Hind III (5 units) at 37° C. for 1 hour.

The plasmid pBY502 (2 μg) prepared in section A) above was digested completely with restriction endonuclease Hind III (1 unit) at 37° C. for 30 minutes.

The digested DNA of the two plasmids were mixed and in order to inactivate the restriction endonucleases, treated at 65° C. for 10 minutes. The components of the inactivated solution were fortified so that as final concentrations, it contained 50 mM Tris buffer (pH 7.6, 10 mM MgCl₂, 10 mM dithiothreitol, 1 mM ATP and 1 units of T4 ligase, and it was incubated at 16° C. for 15 hours. By using this solution, *Escherichia coli* JM109 competent cells (Takara Shuzo Co., Ltd.) were transformed.

The transformants were cultivated at 37° C. for 24 hours in medium L (composition: tryptone 10 g, yeast extract 5 g, NaCl 5 g and 1 liter of deionized water, pH 7.2) containing 30 μg/ml (final concentration) of chloramphenicol, 100 μg/ml (final concentration) of IPTG (isopropyl,β-D-galactopyranoside), 100 μg/ml (final concentration) of X-gal (5-bromo-4-chloro-3-indolyl-β-D-galactopyranoside). From the resulting grown cells, those which grew on white colonies were chosen, and the resulting plasmids were extracted by the alkaline-SDS method [see T. Maniatis, E. F. Fritsh, J. Sambrook, "Molecular Cloning" (1982), 90–91].

D) Transformation of Coryneform Bacteria with Plasmid pCRY2

The transformation was effected by using the ectroporation method. *Brevibacterium flavum* MJ233 (FERM BP-1497) from which the plasmid had been moved was cultivated in 100 ml of the medium A described in section A above till the initial stage of the logarithmic growth period. Penicillin G was added to a concentration of 1 unit/ml, and the cultivation was further continued for 2 hours with shaking. The cells were harvested by centrifugation, and washed with 20 ml of a solution for pulse application composed of 272 mM sucrose, 7 mM KH₂PO₄ and 1 mM MgCl2 (pH 7.4). The cells were further harvested by centrifugation and suspended in 5 ml of the above-mentioned solution for pulse application. The cells (0.75 μl) was mixed with 50 ml of the DNA solution obtained in section C and the mixture was chilled for 20 minutes by ice water. A Gene Pulser (Bio-rad Co.) was used and at 2500 volts and 25 μFD, pulses were applied to the mixture, and then the mixture was chilled for 20 minutes by ice water. All the mixture was transferred to 3 ml of the medium A, and cultivated at 30° C. for 1 hour. The culture was inoculated in the agar plate of medium A as used in section A above containing 3 μg/ml of chloramphenicol (final concentration) at 30° C. for 2 to 3 days. From the chloramphenicol-resistant strains, a plasmid was obtained. The resulting plasmid was digested with various restriction endonuclease, and the results are shown in Table 3.

TABLE 3

| Restriction endonuclease | Number of recognition sites | Molecular weight (megadaltons; kb in the parentheses) |
| --- | --- | --- |
| Hind III | 2 | 2.7 (4.1), 1.4 (2.2) |
| Kpn I | 1 | 4.1 (6.3) |
| EcoR I | 1 | 4.1 (6.3) |
| BamH I | 2 | 2.2 (3.4), 1.9 (2.9) |
| Sma I | 2 | 4.0 (6.1), 0.1 (0.2) |

The plasmid characterized by the above recognition sites by the restriction endonucleases was named "pCRY2".

*Brevibacterium flavum* MJ233 GE101 transformed by the plasmid pCRY2 was deposited at Fermentation Research Institute, Agency of Industrial Science and Technology, Japan, 1-3, Higashi, Tsukuba-shi, Ibaraki-ken, Japan on Jan. 8, 1988 under FERM P-9801 (now transferred to international deposit under the Budapest Treaty as FERM BP-2512 on Jul. 12, 1989).

EXAMPLE 2

Construction of Plasmid pCRY3 Composed of Plasmid pBY503 and plasmid pHSG398, and its Properties

A) Preparation of Plasmid pBY503

Plasmid pBY503 is a plasmid having a molecular weight of 10 megadaltons (about 15 kb) newly isolated from *Brevibacterium stationis* IFO12144 (FERM P-10136 deposited on Jul. 18, 1988 at Fermentation Research Institute, Japan; FERM BP-2515 deposited on Jul. 12, 1989 under the Budapest Treaty). This plasmid is described in Japanese Laid-Open Patent Publication No. 95785/1989. Plasmid pBY503 was prepared by the following procedure.

*Brevibacterium stationis* IFO12144 was cultivated till a later stage of the logarithmic growth period in 1 liter of medium A described in Example 1, section A, and the cells were harvested. The resulting cells were suspended in 20 ml of a buffer [25 mM tris(hydroxymethyl)aminomethane, 10 mM EDTA, and 50 mM glucose] containing lysozyme in a concentration of 10 mg/ml, and incubated at 37° C. for 1 hour. To the reaction solution was added 40 ml of alkaline-SDS solution [0.2N NaOH, 1% (w/v) SDS]. They were gently mixed and allowed to stand at room temperature for 15 minutes.

Then, 30 ml of a potassium acetate solution [a mixture of 60 ml of 5M potassium acetate solution, 11.5 ml of acetic acid, 28.5 ml of deionized water] was added, and after thorough mixing, the mixture was chilled for 15 minutes by ice water.

All the lyzate was transferred to a centrifugal tube, and centrifuged at 4° C. for 10 minutes at 15,000×G to obtain a supernatant.

To the supernatant was added an equal amount of a phenol/chloroform mixture (1:1). The suspension was transferred to a centrifugal tube, and centrifuged at room temperature for 5 minutes at 15,000×G. The aqueous layer was recovered, and mixed with two-fold its amount of ethanol. The mixture was left to stand at −20° C. for 1 hour, and centrifuged at 4° C. for 10 minutes at 15,000×G. The precipitate was recovered.

The precipitate was dried under reduced pressure and then dissolved in 2 ml of a TE buffer [10 mM Tris, 1 mM EDTA, adjusted to pH 8.0 with HCl]. After the dissolving, 15 ml of a cesium chloride solution [a solution prepared by dissolving 170 g of cesium chloride in 100 ml of a TE buffer in a 5-fold concentration] and 1 ml of an ethidium bromide solution (10 mg/ml) were added to the solution, and the density was adjusted to 1.392 g/ml. The solution was centrifuged at 120° C. for 42 hours at 116,000×G.

Plasmid pBY503 was detected in a lower band in the centrifugal tube as a result of ultraviolet irradiation. A solution of a fraction containing plasmid pBY503 was obtained by pulling out this band from the side of the centrifugal tube by using an injection syringe.

This fraction solution was treated four times with an equal amount of isoamyl alcohol to extract and remove ethidium bromide. The residue was then dialyzed against the TE buffer. A 3M sodium acetate solution was added to a final concentration of 30 mM to the resulting dialyzate containing plasmid pBY503, and then ethanol in a two-fold amount was added. The mixture was left to stand at −20° C. for 1 hour. The solution was centrifuged at 15,000×G to precipitate DNA, and about 50 μg of plasmid pBY503 was obtained.

B) Preparation of Plasmid pHSG398

Plasmid pHSG398 replicates in *Escherichia coli*, has a molecular size of about 1.4 megadaltons, and is resistant to chloramphenicol. It is commercially available and can be purchased from Takara Shuzo Co., Ltd.

C) Construction of Plasmid pCRY3

Plasmid pHSG398 (a product of Takara Shuzo Co., Ltd.; 0.5 μg) was digested completely with Kpn I (5 units) at 37° C. for 1 hour.

The plasmid pBY503 (2 μg) prepared in section A above was digested completely with 1 unit of restriction endonuclease Kpn I at 37° C. for 30 minutes.

The both digested plasmids DNA were mixed, and to inactivate the restriction endonucleases, treated at 65° C. for 10 minutes. The components in the inactivated solution were fortified so that it contained, as final concentration, 50 mM Tris buffer (pH 7.6), 10 mM $MgCl_2$, 10 mM dithiothreitol, 1 mM ATP and 1 unit of T4 ligase, and the solution was incubated at 16° C. for 15 hours. *Escherichia coli* JM109 competent cells (a product of Takara Shuzo Co., Ltd.) were transformed by using this solution.

The transformants were cultivated at 37° C. for 24 hours in medium L described in Example 1, section C containing 30 μg/ml (final concentration) of chloramphenicol, 100 μg/ml (final concentration) of IPTG and 100 μg/ml (final concentration) of X-gal, and transformants were obtained. Those transformants which grew in white colonies were selected, and the plasmids were extracted by the alkaline-SDS method described hereinabove.

D) Transformation of Coryneform Bacteria with Plasmid pCRY3

The transformation was carried out by using the electroporation method described in Example 1, section D. From the chloramphenicol-resistant strains which appeared, a plasmid was obtained by using the method described in section A above. This plasmid was digested with various restriction endonucleases, and the molecular sizes of the fragments were measured. The results are shown in Table 4.

TABLE 4

| Restriction endonuclease | Number of recognition sites | Molecular weight (megadaltons; kb in the parentheses) |
|---|---|---|
| Kpn I | 2 | 3.9 (6.0), 1.4 (2.2) |
| Sau I | 1 | 5.3 (8.2) |
| BamH I | 1 | 5.3 (8.2) |
| Pst I | 2 | 3.7 (5.7), 1.6 (2.5) |

The plasmid characterized by the above cleavage sites with the restriction endonucleases was named "pCRY3".

*Brevibacterium flavum* MJ233 GE102 transformed with the compound plasmid pCRY3 was deposited on Jan. 8, 1988 at Fermentation Research Institute, Agency of Industrial Science and Technology, Japan, 1-3, Higashi, Tsukuba-shi, Ibaraki-ken, Japan under FERM P-9802 (transferred to international deposition FERM BP-2513 on Jul. 12, 1989 under the Budapest Treaty).

EXAMPLE 3

Cloning of a 7.4 kb DNA Fragment Encoding the Function of Stabilizing into Plasmids pCRY2 and pCRY3

A) Preparation of a 7.4 kg DNA Fragment Encoding the Stabilizing Function

Plasmid pBY503 was prepared by the method described in Example 2, section A from *Brevibacterium stationis* IFO12144 (FERM BP-2515).

Plasmid pBY503 DNA (20 μg) was digested completely with restriction endonuclease Kpn I (20 units) at 37° C. for 2 hours. The digested DNA was isolated by 0.8% agarose gel electrophoresis, and a DNA fragment having a size of about 7.4 kb was recovered from the gel. DNA was extracted from the fraction, and purified to give about 5 μg of DNA.

B) Cloning of a 7.4 kb DNA Fragment Encoding the Function of Stabilizing into Plasmid pCRY2

The plasmid pCRY2 DNA (1 μg) obtained in Example 1 was digested completely with 5 units of restriction endonuclease Kpn I at 37° C. for 2 hours, and mixed with 2 μg of the DNA fragment prepared in section A above. To inactivate the restriction endonucleases, the mixture was treated at 65° C. for 10 minutes. The components of the inactivated solution were fortified so that as final concentrations, the solution contained 50 mM Tris buffer (pH 7.6), 10 mM MgCl$_2$, 10 mM dithiothreitol, 10 mM ATP and 1 unit of T4 ligase. The mixture was then incubated at 16° C. for 15 hours. *Escherichia coli* HB101 competent cells (a product of Takara Shuzo Co., Ltd.) were transformed with this solution.

The transformants were cultivated at 37° C. for 24 hours in medium L described in Example 1, section C containing chloramphenicol in a final concentration of 30 μg/ml, and were obtained as colonies. From the cells, a plasmid was extracted by the alkaline-SDS method described hereinabove.

C) Transformation of Coryneform Bacteria with Plasmid pCRY21

The transformation was carried out by the strain and the electroporation method described in Example 1, section D. From the chloramphenicol-resistant strain which appeared, a plasmid was obtained by using the method described in Example 1, section A. The plasmid was digested with various restriction endonucleases, and the molecular-weights of the fragments were measured. The results are shown in Table 5.

TABLE 5

| Restriction endonuclease | Number of recognition sites | Molecular weight (megadaltons; kb in the parentheses) |
|---|---|---|
| Kpn I | 2 | 4.1 (6.3), 4.6 (7.0) |
| BamH I | 2 | 6.8 (10.4), 1.9 (2.9) |
| Sau I | 1 | 8.7 (13.3) |
| Pst I | 1 | 8.7 (13.3) |

The plasmid characterized by the fragments with the above restriction endonucleases was named "pCRY21".

D) Cloning of a 7.4 kg DNA Fragment Encoding the Function of Stabilizing into Plasmid pCRY3

The plasmid pCRY3 DNA (1 μg) obtained in Example 2 was digested partially with restriction endonuclease Kpn I (5 units) at 37° C. for 15 minutes. The digested DNA was mixed with 2 μg of the DNA fragment prepared in section A above, and in order to inactivate the restriction endonucleases, the mixture was treated at 65° C. for 10 minutes. The components of the inactivated solution were fortified so that as final concentration, the solution contained 40 mM Tris buffer (pH 7.6), 10 mM dithiothreitol, 1 mM ATP and 1 unit of T4 ligase. The solution was incubated at 16° C. for 15 minutes.

*Escherichia coli* HB101 competent cells were transformed with this solution.

The transformants were cultivated at 37° C. for 24 hours in medium L described in Example 1, section C containing chloramphenicol in a final concentration of 30 μg/ml, and obtained as colonies. From the cells, a plasmid was extracted by the alkaline-SDS method described hereinabove.

E) Transformation of Coryneform Bacteria with Plasmid pCRY31

The transformation was carried out by using the strain and the electroporation described in Example 1, section D. From the chloramphenicol-resistant strains which appeared, a plasmid was obtained by using the method described in Example 1, section A. The plasmid was digested with various restriction endonucleases, and the results are shown in Table 6.

TABLE 6

| Restriction endonuclease | Number of recognition sites | Molecular weight (megadaltons; kb in the parentheses) |
|---|---|---|
| Kpn I | 3 | 4.6 (7.0), 3.9 (6.0), 1.4 (2.2) |
| Sau I | 2 | 6.6 (10.0), 3.3 (5.2) |
| Pst I | 2 | 8.5 (13.0), 1.4 (2.2) |
| BamH I | 1 | 9.9 (15.2) |

The plasmid characterized by the fragments with the above restriction endonucleases was named "pCRY31".

EXAMPLE 4

Cloning of a 2.1 kb DNA Fragment Encoding the Function of Stabilizing into Plasmids pCRY2 and pCRY3

A) Preparation of a 2.1 kb DNA Fragment Encoding the Stabilizing Function

Plasmid pBY503 was prepared from *Brevibacterium stationis* IFO12144 (FERM BP-2515) by the method described in Example 2, section A.

Plasmid pBY503 DNA (20 μg) was digested completely with restriction endonucleases Kpn I and EcoR I (each 20 units) at 37° C. for 2 hours. The digested DNA were separated by 0.8% agarose gel electrophoresis, and a DNA fragment fraction having a size of about 2.1 kb was recovered from the gel. The DNA was extracted from the fraction and purified to give about 5 μg of DNA.

B) Cloning of a 2.1 kb DNA Fragment Encoding the Function of Stabilizing into Plasmid pCRY2

The plasmid pCRY2 DNA (1 μg) obtained in Example 1 was digested completely with restriction endonucleases Kpn I and EcoR I (5 units) at 37° C. for 2 hours. The digested DNA was mixed with 2 μg of the DNA fragment prepared in section A above. To inactivate the restriction endonucleases, the mixture was treated at 65° C. for 10 minutes. The components of the inactivated solution were fortified so that as final concentrations, the solution contained 50 mM Tris buffer (pH 7.6), 10 mM MgCl$_2$, 10 mM dithiothreitol, 1 mM ATP and T4 ligase (1 unit). The solution was incubated at 16° C. for 15 hours. *Escherichia coli* HB101competent cells (a product of Takara Shuzo Co., Ltd.) were transformed by using this solution.

The transformants were cultivated in medium L described in Example 1, section C containing chloramphenicol in a final concentration of 30 μg/ml at 37° C. for 24 hours, and obtained as colonies. From the cells, a plasmid was extracted by the alkaline-SDS method described hereinabove.

C) Transformation of Coryneform Bacteria with Plasmid pCRY2KE

The transformation was carried out by using the strain and the electroporation method described in Example 1, section D. A plasmid was obtained by the method described in Example 1, section A from the chloramphenicol-resistant strains that appeared. The plasmid was digested with various restriction endonucleases, and the molecular weights of the fragments were measured. The results are shown in Table 7.

TABLE 7

| Restriction endonuclease | Number of recognition sites | Molecular weight (megadaltons; kb in the parentheses) |
| --- | --- | --- |
| Sac I | 2 | 4.2 (6.5), 1.2 (1.9) |
| Hind III | 3 | 2.7 (4.1), 1.7 (2.7), 1.0 (1.6) |
| Kpn I | 1 | 5.4 (8.4) |
| EcoR I | 1 | 5.4 (8.4) |

The plasmid characterized by the fragments with the above restriction endonucleases was named "pCRY2KE".

D) Cloning of a 2.1 kb DNA Fragment Encoding the Function of Stabilizing into Plasmid pCRY3

The plasmid pCRY3 DNA (1 μg) obtained in Example 2 was digested partially with restriction endonucleases Kpn I and Eco RI (5 units) at 37° C. for 15 minutes. The partially digested DNA was mixed with 2 g of the DNA fragment prepared in section A above, and the mixture was treated at 65° C. for 15 minutes to inactivate the restriction endonucleases. The components of the inactivated solution were fortified so that as final concentrations, the solution contained 50 mM Tris buffer (pH 7.6), 10 mM MgCl$_2$, 10 mM dithiothreitol, 1 mM ATP and 1 unit of T4 ligase. The solution was then incubated at 16° C. for 15 minutes. By using the solution, *Escherichia coli* HB101 competent cells (a product of Takaro Shuzo Co., Ltd.) were transformed.

The transformants were cultivated in medium L described in Example 1, section C containing chloramphenicol in a final concentration of 30 μg/ml, and obtained as colonies. From the cells, a plasmid was extracted by the alkaline-SDS method described hereinabove.

E) Transformation of Coryneform Bacteria with Plasmid pCRY3KE

The transformation was carried out by using the strain and the electroporation method described in Example 1, section D. From the chloramphenicol-resistant strains that appeared, a plasmid was obtained by the same alkaline-SDS method as described above. The plasmid was digested with various restriction endonucleases, and the molecular weights of the fragments were measured. The results are shown in Table 8.

TABLE 8

| Restriction endonuclease | Number of recognition sites | Molecular weight (megadaltons; kb in the parentheses) |
| --- | --- | --- |
| Kpn I | 2 | 3.9 (6.0), 2.8 (4.3) |
| Sma I | 2 | 5.9 (9.0), 0.8 (1.3) |
| EcoR I | 2 | 3.4 (5.3), 3.3 (5.0) |
| BamH I | 1 | 6.7 (10.3) |

The plasmid characterized by the fragments with the above restriction endonucleases was named "pCRY3KE".

EXAMPLE 5

Cloning of a 1763 Bp DNA Fragment Encoding the Function of Stabilizing into Plasmids pCRY2 and pCRY3

A) Preparation of a 1763 Bp DNA Fragment Encoding the Stabilizing Function

Plasmid pRY503 was prepared from *Brevibacterium stationis* IF012144 (FERM BP-2515) by the method described in Example 2, section A.

Plasmid pBY503 DNA (20 μg) was digested completely with restriction endonucleases Kpn I and Xba I (each 20 units) at 37° C. for 2 hours. The digested DNA was separated by 0.8% agarose gel electrophoresis, and the 1763 bp DNA fragment fraction was recovered from the gel. DNA was extracted from the fraction, and purified to give about 5 μg of DNA.

The total nucleotide sequence of the resulting DNA was determined by the dideoxy chain termination method [F. Sanger et al., Proc. Natl. Acad. Sci., U.S.A. 74, p. 5463 (1977)] by using pUC18 or pUC19 [Messing, J. and Vieira, J: Gene 19, p. 269 (1982)].

B) Cloning of a 1763 bp DNA Fragment Encoding the Function of Stabilizing Into Plasmid pCRY2

Plasmid pCRY2 DNA (1 μg) obtained in Example 1 was digested completely with restriction endonucleases Kpn I and Xba I (5 units) at 37° C. for 2 hours. The digested DNA was mixed with 2 μg of the DNA fragment prepared in section A above and, in order to inactivate the restriction endonucleases, the mixture was treated at 65° C. for 10 minutes. The components of the inactivated solution were fortified so that as final concentrations, the solution contained 50 mM Tris buffer (pH 7.6), 10 mM MgCl$_2$, 10 mM dithiothreitol, 1 mM ATP and 1 unit of T4 ligase. The mixture was then incubated at 16° C. for 15 hours. By using this solution, *Escherichia coli* HB101 competent cells (a product of Takara Shuzo Co., Ltd.) were transformed.

The transformants were cultivated at 37° C. for 24 hours in medium L described in Example 1, section C containing chloramphenicol in a final concentration of 30 μg, and obtained as colonies. From the cells obtained, a plasmid was extracted by the alkaline-SDS method described hereinabove. C) Transformation of Coryneform Bacteria with Plasmid pCRY2KX The transformation was carried out by using the strain and the electroporation method described in Example 1, section D. From the chloramphenicol-resistant strains that appeared, a plasmid was obtained by using the alkali-SDS method described above. The plasmid was digested with various restriction endonucleases, and the molecular weights of the fragments were measured. The results are shown in Table 9.

TABLE 9

| Restriction endonuclease | Number of recognition sites | Molecular weight (megadaltons; kb in the parentheses) |
| --- | --- | --- |
| Hind III | 3 | 2.7 (4.1), 2.3 (3.5), 0.2 (0.4) |
| Sac I | 2 | 2.8 (4.3), 2.4 (3.7) |
| EcoR I | 1 | 5.2 (8.0) |
| Kpn I | 1 | 5.2 (8.0) |

The plasmid characterized by the fragments with the above restriction endonucleases was named "pCRY2KX".

D) Cloning of a 1763 bp DNA Fragment Encoding the Function of Stabilizing into Plasmid pCRY3

Plasmid pCRY3 DNA (1 μg) obtained in Example 2 was digested partially with restriction endonucleases Kpn I and Xba I (5 units) at 37° C. for 2 hours. The digested DNA product was mixed with 2 μg of the DNA prepared in section A above, and to inactivate the restriction endonucleases, the mixture was treated at 65° C. for 10 minutes. The components of the inactivated solution were fortified so that the solution contained, as final concentration, 50 mM Tris buffer (pH 7.6), 10 mM MgCl$_2$, 10 mM dithiothreitol, 1 mM ATP and 1 unit of T4 ligase, and the solution was incubated at 16° C. for 15 minutes. By using this solution, *Escherichia coli* HB101 competent cells (a product of Takara Shuzo Co., Ltd.) were transformed.

The transformants were cultivated at 37° C. for 24 hours in medium L described in Example 1, section C containing chloramphenicol in a final concentration of 30μg/ml, and obtained as colonies. From the cells, a plasmid was extracted by the alkaline-SDS method described hereinabove.

E) Transformation of Coryneform Bacteria with Plasmid pCRY3KX

The transformation was carried out by using the strain and the electroporation method described in Example 1, section D. From the chloramphenicol-resistant strains that appeared, a plasmid was obtained by the method described in Example 1, section A. The plasmid was digested with various restriction endonucleases, and the molecular weights of the fragments were measured. The results are shown in Table 10.

TABLE 10

| Restriction endonuclease | Number of recognition sites | Molecular weight (megadaltons; kb in the parentheses) |
| --- | --- | --- |
| EcoR I | 2 | 3.6 (5.5), 2.9 (4.4) |
| Sac I | 2 | 4.4 (6.7), 2.1 (3.2) |
| Kpn I | 2 | 3.9 (6.0), 2.6 (3.9) |
| Sma I | 1 | 6.5 (9.9) |

The plasmid characterized by the fragments with the above restriction endonucleases was named "pCRY3KX".

EXAMPLE 6

Stability of Constructed Plasmids

Strains derived from *Brevibacterium flavum* MJ233 containing the plasmids pCRY2, pCRY21, pCRY2KE, pCRY2KX, pCRY3, pCRY31, pCRY3KE and pCRY3KX were each inoculated in the medium A described in Example 1, section A containing 5 μg/ml (final concentration) of chloramphenicol, and pre-cultivated at 30° C. for 15 hours. Then, the culture was transferred to a fresh supply of the medium A described in Example 1, section A at rate of $10^4$ cells per ml, and subcultivated through about 100 generations. The number of chloramphenicol-resistant cells (plasmid-containing cells) in the culture based on the total number of cells for each strain was determined. The results are shown in Table 11.

TABLE 11

| Cultured Strain | Plasmid-containing cells of cultured strain (%) |
| --- | --- |
| pCRY2 (FERM BP-2512) | <1 |
| pCRY21 | >95 |
| pCRY2KE | >95 |
| pCRY2KX | >95 |
| pCRY3 (FERM BP-2513) | 20 |
| pCRY31 | >95 |
| pCRY3KE | >95 |
| pCRY3KX | >95 |

Some specific examples of molecular breeding of Coryneform bacteria using the plasmid vectors of the invention will be shown below. It should be understood that these examples are given as an aid to a specific recognition of the utility and application of this invention, and do not in any way limit the scope of the invention.

EXAMPLE A

Cloning of the DNA Region Containing a Gene (Trp Gene) Encoding Tryptophan Synthase into Plasmids pCRY31, pCRY3KE and pCRY3KX, and the Production of L-tryptophan by Coryneform Bacteria Transformed with these Plasmids (1) Preparation of a DNA Region Containing a Gene (Trp Gene) Encoding the Tryptophan Synthase A) Preparation of Phage φ80 pt

*Escherichia coli* K-12 (IF03301) was inoculated in 100 ml of the medium L described in Example 1, C), and cultivated with shaking at 37° C. for about 4 hours. Then, 0.2 ml of the culture was mixed with 0.1 ml of an aqueous solution of phage φ80 ($10^5$/ml) in medium L soft agar (L medium+agar), and overlaid on an medium L agar plate. When the plate was incubated at 37° C. for about 5 hours, plaques occurred. When the incubation was continued at 37° C. for 2 to 3 days, grown colonies of phage φ80 lysogenic bacteria formed in the plaques. The lysogenic phage was cultivated in medium L at 37° C. for 4 hours, and then coated on the same medium L agar plate as above. Then by induction of the lysogenic phage through ultraviolet irradiation (400–800 ergs/mm$^2$, 10–20 seconds), phage φ80 pt (a phage DNA containing a tryptophan operon) was prepared.

B) Preparation of a Tryptophan Operon Fraction

*Escherichia coli* K-12 (IF03301) was inoculated in 1 liter of medium L having the same composition as described above, and cultivated at about 37° C. for about 3 hours. In the logarithmic growth period, 10 ml of a 25% (w/v) glucose solution and the phage φ80 pt solution prepared above in a concentration of (multiple of infection 20) were added. The shaking was continued for 5 hours, and then in a conventional manner, chloroform was added to prepare a large quantity of phage φ80 pt [see T. Maniatis, E. F. Fritsch, Sambrook: "Molecular Cloning" (1982), pages 76-80, Cold Spring Harbor Laboratory].

The phage φ80 pt solution prepared above was dialyzed against Tris buffer (pH 7.8), and by the DNA extracting method using phenol [see "Molecular Cloning", p. 85], phage DNA was extracted and purified. It was digested with restriction endonuclease BamH I at 30° C. for 30 minutes to give a tryptophan operon gene fraction.

C) Preparation of Plasmid pBR322Trp

The tryptophan operon fraction obtained in section B above was digested with restriction endonucleases Sal I and Xho I at 37° C. for 1 hour, and the reaction mixture was heat-treated at 65° C. for 5 hours to deactivate the restriction endonucleases. The digested DNA was mixed with plasmid pBR322 (a product of Takara Shuzo Co., Ltd.) treated in the same way as above with restriction endonuclease Sal I. Then, the components of the inactivated solution were fortified so that as final concentrations, the solution contained 50 mM Tris buffer (pH 7.6), 10 mM MgCl$_2$, 10 mM dithiothreitol, 1 mM ATP and 1 unit of T$_4$ ligase, and the solution was incubated at 16° C. for 15 hours to ligate the DNA.

Using the DNA after re-ligation, *Escherichia coli* K-12 (tryptophan-requiring mutant, ATCC23718) was transformed by a conventional method to obtain a transformant [characterized by a disappearance of the Trp requiring property; it became bio-synthesizable by trp A and trp B genes on the plasmid, and became growable on a minimum essential medium (K 7 g, KH 2 g, MgSO$_4$.7H$_2$O 0.1 g, (NH$_4$)$_2$SO$_4$ 1 g, glucose 2 g, deionized water 1 liter)]. This transformant was cultivated in a liquid medium in accordance with a conventional method, and plasmid pBR322 trp was isolated from the culture and purified.

D) Cloning of Trp AB Fraction into Plasmid pDR720

The plasmid pBR322trp obtained in section C above was digested with restriction endonucleases Sac II and Sal I at 37° C. for 1 hour to give a fraction containing the trp AB gene. Then, the fraction was digested partially with restriction endonuclease Hinc II at 37° C. to give a minimum fraction containing trp AB. This fragment was mixed with a Sal I linker and ligated with a T$_4$ DNA ligase to give a trp AB fraction having a Sal I site at both ends.

Plasmid pDR720 (a product of Pharmacia Co.) was digested with restriction endonuclease Sal I at 37° C. for 1 hour. The reaction mixture was treated at 65° C. for 5 minutes to inactivate the restriction endonuclease. The inactivated solution was mixed with the trp AB fraction.

The components of the inactivated solution were fortified so that as final concentrations, the solution contained 50 mM Tris buffer (pH 7.6), 10 mM dithiothreitol, 10 mM MgCl$_2$, 1 mM ATP and 1 unit of T$_4$ ligase. The solution was incubated at 16° C. for 15 hours to ligate the DNA.

By using the DNA after re-ligating, *Escherichia coli* K-12 (tryptophan-requiring mutant, ATCC23718) was transformed to give a transformant [characterized by an disappearance of the trp requiring property; it became bio-synthesizable by trp A and trp B genes on the plasmid, and became growable on a minimum essential medium (K 7 g, KH$_2$PO$_4$ 2 g, MgSO$_4$.7H$_2$O 0.1 g, 2SO$_4$ 1 g, glucose 2 g, deionized water 1 liter)]. This transformant was cultivated in a liquid medium in a customary manner, and plasmid pDR720 trp AB was isolated from the culture and purified.

E) Cloning of Trp AB Gene into Plasmid pUC9

The plasmid pDR720 trp AB obtained in section D above was digested with restriction endonuclease EcoR I at 37° C. for 1 hour, and the reaction mixture was treated at 65° C. for 5 minutes to inactivate the restriction endonuclease. Likewise, plasmid pUC9 (a product of Pharmacia Co.) was treated with restriction endonuclease EcoR I, and ligated with the plasmid pDR720 trp AB DNA. *E. coli* was likewise transformed with the DNA after re-ligation. From the resulting strains, those having plasmid pUC9 containing the trp AB fraction were selected. Plasmid pUC9 trp AB was extracted by a conventional method from the selected strains.

(2) Cloning of a DNA Region Containing a Gene (Trp Gene) Encoding the Tryptophan Synthase into Plasmids pCRY31, pCRY3KE and pCRY3KX A) Construction of Plasmids pCRY31trpl, pCRY3KE trpl and pCRY3KXtrpl The plasmid pUC9trp AB (10 g) prepared in section (1), D and 3 μg of each of the plasmids pCRY31, pCRY3KE and pCRY3KX were digested with BamH I at 37° C. for 1 hour. The reaction mixture was treated at 65° C. for 10 minutes to inactivate the restriction endonuclease. The components of the inactivated solution were fortified so that the solution contained, as final concentrations, 50 mM tris buffer (pH 7.6), 10 mM MgCl$_2$, 10 mM dithiothreitol, 1 mM ATP and 1 unit of T$_4$ ligase. The solution was incubated at 16° C. for 15 hours to ligate the DNA. By using this solution, *Escherichia coli* HB101 competent cells were transformed. As a control, the same operation as above was carried out by using plasmid pCRY3 prepared in Example 2.

The transformant was cultivated at 37° C. for 24 hours in medium L described in Example 1, section C containing chloramphenicol in a final concentration of 30 μg/ml, and obtained as colonies. From the cells, a plasmid was extracted by the alkaline-SDS method described hereinabove.

B) Transformation of Coryneform Bacteria with Constructed Plasmids

The transformation with the plasmids constructed in section A above was carried out by using the same strain and the same electoporation method as described in Example 1, section D. From the chloramphenicol-resistant strain, a plasmid was obtained by using the method described in section A. The plasmid pCRY31 into which trp gene was cloned was digested with various restriction endonucleases and the molecular weights of the fragments were measured. The results are shown in Table 12.

TABLE 12

| Restriction endonuclease | Number of recognition sites | Molecular weight (megadaltons; kb in the parentheses) |
|---|---|---|
| BamH I | 2 | 9.9 (15.2), 1.8 (2.8) |
| Sau I | 2 | 6.6 (10.0), 5.1 (8.0) |
| Pst I | 2 | 10.3 (15.8), 1.4 (2.2) |

The plasmid characterized by the fragments with the above restriction endonucleases was named "pCRY31trpl".

Brevibacterium flavum MJ233 GE1004 transformed with plasmid pCRY31trpl was deposited at Fermentation Research Institute, Agency of Industrial Science and Technology, Japan, 1-3, Higashi, Tsukuba-shi, Ibaraki-ken, Japan, on May 26, 1988 under deposite No. FERM P-10035 [transferred to international deposit (FERM BP-2514) on July 12, 1989 under the Budapest Treaty].

The trp gene was cloned into plasmid pCRY3KE. The resulting plasmid was digested with various restriction endonucleases, and the molecular weights of the resulting fragments were measured. The results are shown in Table 13.

TABLE 13

| Restriction endonuclease | Number of recognition sites | Molecular weight (megadaltons; kb in the parentheses) |
| --- | --- | --- |
| BamH I | 2 | 6.7 (10.3), 1.8 (2.8) |
| Kpn I | 2 | 4.6 (7.1), 3.9 (6.0) |
| Sau I | 1 | 8.5 (13.1) |

The plasmid characterized by the fragments with the above restriction endonucleases was named "pCRY3-KEtrpl".

The trp gene was cloned into plasmid pCRY3KX, and the plasmid was digested with various restriction endonucleases. The molecular weights of the resulting fragments were measured, and the results are shown in Table 14.

TABLE 14

| Restriction endonuclease | Number of recognition sites | Molecular weight (megadaltons; kb in the parentheses) |
| --- | --- | --- |
| BamH I | 2 | 6.5 (9.9), 1.8 (2.8) |
| Sau 1 | 1 | 8.3 (12.7) |
| Kpn I | 2 | 4.4 (6.7), 3.9 (6.0) |

The plasmid characterized by the fragments with the above restriction endonuclease was named "pCRY3KXtrpl".

As a control, the trp gene was further cloned into a control plasmid pCRY3. The resulting plasmid was digested with various restriction endonucleases. The molecular weights of the resulting fragments were measured, and the results are shown in Table 15.

TABLE 15

| Restriction endonuclease | Number of recognition sites | Molecular weight (megadaltons; kb in the parentheses) |
| --- | --- | --- |
| BamH I | 2 | 5.3 (8.2), 1.8 (2.8) |
| Sau I | 1 | 7.1 (11.0) |
| Kpn I | 2 | 3.9 (6.0), 3.2 (5.0) |

The plasmid characterized by the fragments with the above restriction endonucleases was named "pCRY3trpl".

(3) Stability of Plasmids pCRY31trpl, pCRY3KEtrpl and pCRY3KXtrpl

The medium A described in Example 1, section A (100 ml) was put in a 500 ml Erlenmeyer flask, and sterilized at 120° C. for 15 minutes. Each of the transformants obtained in section (2), B) was inoculated in the sterilized medium A and cultivated at 30° C. for 24 hours with shaking. The culture was inoculated in a fresh supply of 100 ml of the medium A sterilized at 120° C. for 15 minutes in a 500 ml Erlenmeyer flask. The density of the culture transferred to the fresh medium A was 50 cells per ml. The transferred culture was cultivated with shaking at 30° C. for 24 hours. Then, the cells were harvested by centrifugal separation, washed, and spreaded in a fixed amount on an agar plate medium A prepared as medium A containing 5 µg/ml of chloramphenicol and a medium A free from chloramphenicol, and after cultivation at 30° C. for 1 day, the grown colonies were counted.

It was consequently found that the number of colonies which grew on the chloramphenicol-containing medium A was equal to that in the chloramphenicol-free medium A, and the colonies grown on the medium A grew on the chloramphenicol-containing medium A. In other words, the high stability of the plasmids pCRY31trpl, pCRY3KEtrpl and pCRY3KXtrpl could be determined.

With the control plasmid pCRY3trpl, the number of colonies grown on the chloramphenicol-containing medium A was about 10% of that of colonies grown on the drug-free medium A.

(4) Production of L-tryptophan by Using Coryneform Bacteria Transformed with the Plasmid pCRY31trpl, pCRY3KEtrpl or pCRY3KXtrpl 100 ml of a culture medium (urea 0.4%, ammonium sulfate 1.4%, KH 0.5%, K 0.05%, MgSO$_4$.7H$_2$O 0.05%, CaCl$_2$2H$_2$O 2 ppm, FeSO$_4$.7H$_2$O 2 ppm, MnSO$_4$.4-6H$_2$O 2 ppm, ZnSO$_4$.7H$_2$O 2 ppm, NaCl 2 ppm, biotin 200 µg/liter, thiamine hydrochloride 100 µg/liter, tryptone 0.1%, yeast extract 0.1%) was put in a 500 ml Erlenmeyer flask and then sterilized (pH 7.0 after sterilization). The above transformants containing plasmids pCRY31trpl, pCRY3KEtrpl, pCRY3KXtrpl and control plasmid pCRY3trpl were each inoculated in the medium, and after aseptically adding glucose so as to provide a final concentration of 2% (w/v), cultivated with shaking at 30° C. for 15 hours.

Then, 1000 ml of a main culture medium (ammonium sulfate 2.3%, KH$_2$PO$_4$ 0.05%, K$_2$HPO$_4$ 0.05%, MgSO$_4$.7H$_2$O 0.05%, FeSO$_4$.7H$_2$O 20 ppm, MnSO$_4$.n-H$_2$O 20 ppm, biotin 200µg/liter, thiamine hydrochloride 100 µg/liter, tryptone 9.3%, yeast extract 0.3%) was introduced into 2 liter aeration stirring vessel, and sterilized at 120° C. for 20 minutes, and aseptically, glucose was added in a final concentration of 2% (w/v). Furthermore, 20 ml of the preculture was added, and cultivated at a rotation speed of 1000 rpm, a temperature of 33° C. and a pH of 7.4 for 18 hours with an aeration amount of 1 vvm.

Glucose was added intermittently at intervals of 1 to 2 hours so that its concentration in the medium during cultivation did not exceed 2% by weight.

After the cultivation, the cells were harvested by centrifugation of 400 ml of the culture, washed twice with deionized water, and suspended in 1,000 ml of a reaction solution [indole 5 g, DL-serine 20 g, pyridoxal-5'-phosphoric acid 10 mg, KCl 2 g, distilled water, 1,000 ml; adjusted to pH 8.0 with 5N-KOH]. The suspension was introduced into a 2-liter aeration stirring tank, and the reaction was carried out at 37° C., 300 rpm and pH 8.0 for 10 hours. After the reaction, a supernatant was prepared from the reaction mixture by centrifugation (6000 rpm, 15 minutes, 4° C.). L-tryptophan in the supernatant was measured by liquid chromatography.

500 ml of the reaction mixture after the reaction was passed through a column of an ammonia-type strongly basic ion exchange resin ("Diaion Sk-1B", a product of Mitsubishi Chemical Co., Ltd.) for the purification of L-tryptophan. The column was eluted, and the eluate was concentrated to precipitate crystals of L-tryptophan.

The results are shown in Table 16.

TABLE 16

| Strain | Concentration of the productd formed (g/liter) | Amount of the product purified (g/liter) |
|---|---|---|
| Strain harboring pCRY3ltrpl (FERM BP-2514) | 3.0 | 1.0 |
| Strain harboring pCRY3KEtrpl | 3.3 | 1.1 |
| Strain harboring pCRY3KXtrpl | 3.5 | 1.4 |
| Strain harboring pCRY3trpl | 0.05 | — |

EXAMPLE B

Cloning of the DNA Region Containing a Gene (Tna A Gene) Encoding Tryptophanase into Plasmids pCRY31, pCRY3KE and pCRY3KX, and the Production of L-tryptophan by Coryneform Bacteria Transformed with These Plasmids (1) Preparation of a DNA Region Containing a Gene (Tna A Gene) Encoding Tryptophanase A) Preparation of a Tryptophanase Gene Fraction

*Escherichia coli* K-12 (IFO3301) was innoculated in 100 ml of the medium L described in Example 1, section C, and cultivated with shaking at 37° C. for about 4 hours. Then, the cells were harvested and a chromosomal DNA was extracted and purified by known method [see H. Saito and K. Miura, Biochim. Biophys. Acta., Vol. 72, p. 619 (1963)]. The extracted chromosomal DNA was digested with restriction endonucleases BamH I and Hind III at 37° C. for 1 hour to give a tryptophanase gene fraction.

B) Preparation of Plasmid pBR322tna

Plasmid pBR322 (a product of Takara Shuzo Co., Ltd.) was digested with restriction endonucleases BamH I and Hind III at 37° C. for 1 hour and mixed with tryptophanase gene fraction which was obtained in section A above. Then, the mixture was heat-treated at 65° C. for 10 minutes to inactivate the restriction endonucleases. Then, the components of the inactivated solution were fortified so that as final concentrations, the solution contained 50 mM Tris buffer (pH 7.6), 10 mM $MgCl_2$, 10 mM dithiothreitol, 1 mM ATP and 1 unit of $T_4$ ligase, and the solution was incubated at 16° C. for 15 hours to ligate the DNA.

Using the DNA after re-ligation, *Escherichia coli* K-12 (tryptophan-requiring mutant, ATCC23718) was transformed by a conventional method to obtain a transformant [characterized by a disappearance of the Trp requiring property; it became bio-synthesizable by tna A gene on the plasmid and become growable on a minimum essential medium ($K_2HPO_4$ 7 g, $KH_2PO_4$ 2 g, $MgSO_4.7H_2O$ 0.1 g, $(NH_4)_2SO_4$ 1 g, glucose 2 g, deionized water 1 liter)]. This transformant was cultivated in a liquid medium in accordance with a conventional method, and plasmid pBR322tna was isolated from the culture and purified.

(2) Cloning of a DNA Region Containing a Gene (Tna A Gene) Encoding Tryptophanase into Plasmids pCRY31, pCRY3KE and pCRY3KX A) Construction of Plasmids pCRY3tna, PCRY3KEtna and pCRY3KXtna The plasmid pBR322tna was digested with restriction endonuclease Hind III at 37° C. for 1 hour. The reaction mixture was heat-treated at 65° C. for 10 minutes to inactivate the restriction endonuclease. And then, recessed 3' end of the digested plasmid was filled with klenow fragment to produce blunt end [see T. Maniatis, E. F. Fritsch and J. Sambrook; "Molecular Cloning" (1982), 113-114, Cold Spring Harbor Laboratory]. After the fill-in reaction, a BamH I linker (5'CCGGATCCGG3') (a product of Takara Shuzo Co., Ltd.) was ligated to the end of the digested plasmid by known method [See T. Maniatis, E. F. Fritsch and J. Sambrook; "Molecular Cloning" (1982), 125-126, Cold Spring Harbor Laboratory]. Then, the linear plasmid DNA ligated with BamH I linker was digested with restriction endonuclease BamH I at 37° C. for 1 hour. The reaction mixture was loaded into 0.8% agarose gel electrophoresis to isolate the 3.2 kb tryptophanase gene fraction.

Each of the plasmids pCRY31, pCRY3KE and pCRY3KX was digested with restriction endonuclease BamH I at 37° C. for 1 hour. The reaction mixture was heat-treated at 65° C. for 10 minutes to inactivate the restriction endonuclease. The 3.2 kb tryptophanase gene fraction which was obtained above was added to the inactivated solution. Then, the components of the solution were fortified so that the solution contained, as final concentrations, 50 mM tris buffer (pH 7.6), 10 mM $MgCl_2$, 10 mM dithiothreitol, 1 mM ATP and 1 unit of $T_4$ ligase. The solution was incubated at 16° C. for 15 hours to ligate the DNA. By using this solution, *Escherichia coli* HB101 competent cells were transformed. As a control, the same operation as above was carried out by using plasmid pCRY3 prepared in Example 2.

The transformant was cultivated at 37° C. for 24 hours in medium L described in Example 1, section C containing chloramphenicol in a final concentration of 30 μg/ml, and obtained as colonies. From the cells, a plasmid was extracted by the alkaline-SDS method described hereinabove.

B) Transformation of Coryneform Bacteria with Constructed Plasmids

The transformation with the plasmids constructed in section A above was carried out by using the same strain and the same electroporation method as described in Example 1, section D. From the chloramphenicol-resistant strain, a plasmid was obtained by using the method described in section A. The plasmid pCRY31 into which tna A gene was cloned was digested with various restriction endonucleases and the molecular weights of the fragments were measured. The results are shown in Table 17.

TABLE 17

| Restriction endonuclease | Number of recognition sites | Molecular weight (megadaltons; kb in the parentheses) |
|---|---|---|
| BamH I | 2 | 9.1 (15.2), 1.9 (3.2) |
| Sac I | 2 | 7.0 (11.7), 4.0 (6.7) |

TABLE 17-continued

| Restriction endonuclease | Number of recognition sites | Molecular weight (megadaltons; kb in the parentheses) |
|---|---|---|
| EcoR I | 5 | 6.1 (10.4), 1.7 (2.8), 1.6 (2.6), 1.5 (2.5), 0.1 (0.1) |

The plasmid characterized by the fragments with the above restriction endonucleases was named "pCRY31tna".

*Brevibacterium flavum* MJ233 GE1006 transformed with plasmid pCRY31tna was deposited at Fermentation Research Institute, Agency of Industrial Science and Technology, Japan, 1-3, Higashi, Tsukuba-shi, Ibaraki-ken, Japan, on Jan. 19, 1988 under deposit No. FERM P-10486 [transferred to international deposit (FERM BP-2717) on Jan. 8, 1990 under the Budapest Treaty].

The tna A gene was cloned into plasmid pCRY3KE. The resulting plasmid was digested with various restriction endonucleases, and the molecular weights of the resulting fragments were measured. The results are shown in Table 18.

TABLE 18

| Restriction endonuclease | Number of recognition sites | Molecular weight (megadaltons; kb in the parentheses) |
|---|---|---|
| BamH I | 2 | 6.2 (10.3), 1.9 (3.2) |
| Sac I | 2 | 8.1 (13.5) |
| EcoR I | 1 | 4.9 (8.2), 3.2 (5.3) |

The plasmid characterized by the fragments with the above restriction endonucleases was named "pCRY3-KEtna".

The tna A gene was cloned into plasmid pCRY3KX, and the plasmid was digested with various restriction endonucleases. The molecular weights of the resulting fragments were measured, and the results are shown in Table 19.

TABLE 19

| Restriction endonuclease | Number of recognition sites | Molecular weight (megadaltons; kb in the parentheses) |
|---|---|---|
| BamH I | 2 | 5.9 (9.9), 1.9 (3.2) |
| EcoR I | 2 | 5.2 (8.7), 2.6 (4.4) |
| Sac I | 2 | 5.9 (9.9), 1.9 (3.2) |

The plasmid characterized by the fragments with the above restriction endonuclease was named "pCRY3KXtna".

As a control, the tna A gene was further cloned into a control plasmid pCRY3. The resulting plasmid was digested with various restriction endonucleases. The molecular weights of the resulting fragments were measured, and the results are shown in Table 20.

TABLE 20

| Restriction endonuclease | Number of recognition sites | Molecular weight (megadaltons; kb in the parentheses) |
|---|---|---|
| BamH I | 2 | 4.9 (8.2), 1.9 (3.2) |
| EcoR I | 2 | 3.5 (5.9), 3.3 (5.5) |
| Sac I | 1 | 6.8 (11.4) |

The plasmid characterized by the fragments with the above restriction endonucleases was named "pCRY3tna".

(3) Stability of Plasmids pCRY31tna, pCRY3KEtna and pCRY3KXtna

The medium A described in Example 1, section A (100 ml) was put in a 500 ml Erlenmeyer flask, and sterilized at 120° C. for 15 minutes. Each of the transformants obtained in section (2), B) was inoculated in the sterilized medium A and cultivated at 30° C. for 24 hours with shaking. The culture was inoculated in a fresh supply of 100 ml of the medium A sterilized at 120° C. for 15 minutes in a 500 ml Erlenmeyer flask. The density of the culture transferred to the fresh medium A was 50 cells per ml. The transferred culture was cultivated with shaking at 30° C. for 24 hours. Then, the cells were harvested by centrifugal separation, washed, and spreaded in a fixed amount on an agar plate medium A prepared as medium A containing 5 µg/ml of chloramphenicol and a medium A free from chloramphenicol, and after cultivation at 30° C. for 1 day, the grown colonies were counted.

It was consequently found that the number of colonies which grew on the chloramphenicol-containing medium A was equal to that in the chloramphenicol-free medium A, and the colonies grown on the medium A grew on the chloramphenicol-containing medium A In other words, the high stability of the plasmids pCRY31tna, pCRY3KEtna and pCRY3KXtna could be determined.

With the control plasmid pCRY3tna, the number of colonies grown on the chloramphenicol-containing medium A was about 10% of that of colonies grown on the drug-free medium A.

(4) Production of L-tryptophan by Using Coryneform Bacteria Transformed with the Plasmid pCRY31tna, pCRY3KEtna or pCRY3KXtna 100 ml of a culture medium (urea 0.4%, $MgSO_4 \cdot 7H_2O$ 0.05%, $CaCl_2 \cdot 2H_2O$ 2 ppm, $FeSO_4 \cdot 7H_2O$ 2 ppm, $MnSO_4 \cdot 4-6H_2O$ 2 ppm, $ZnSO_4 \cdot 7H_2O$ 2 ppm, NaCl 2 ppm, biotin 200 µg/liter, thiamine hydrochloride 100 µg/liter, tryptone 0.1%, yeast extract 0.1%) was put in a 500 ml Erlenmeyer flask and then sterilized (pH- 7.0 after sterilization). The above transformants containing plasmids pCRY31tna, pCRY3KEtna, pCRY3KXtna and control plasmid pCRY3tna were each inoculated in the medium, and after aseptically adding glucose so as to provide a final concentration of 2% (w/v), cultivated with shaking at 30° C. for 15 hours.

Then, 1000 ml of a main culture medium (ammonium sulfate 2.3%, $KH_2PO_4$ 0.05%, $K_2HPO_4$ 0.05%, $MgSO_4 \cdot 7H_2O$ 0.05%, $FeSO_4 \cdot 7H_2O$ 20 ppm, $MnSO_4 \cdot nH_2O$ 20 ppm, biotin 200 µg/liter, thiamine hydrochloride 100 µg/liter, tryptone 9.3%, yeast extract 0.3%) was introduced into 2 liter aeration stirring vessel, and sterilized at 120° C. for 20 minutes, and aseptically, glucose was added in a final concentration of 2% (w/v). Furthermore, 20 ml of the preculture was added, and cultivated at a rotation speed of 1000 rpm, a temperature of 33° C. and a pH of 7.4 for 18 hours with an aeration amount of 1 vvm.

Glucose was added intermittently at intervals of 1 to 2 hours so that its concentration in the medium during cultivation did not exceed 2% by weight.

After the cultivation, the cells were harvested by centrifugation of 400 ml of the culture, washed twice with deionized water, and suspended in 1,000 ml of a reaction solution indole 5 g, DL-serine 20 g, pyridoxal- 5'-phosphoric acid 10 mg, KCl 2 g, distilled water 1,000 ml; adjusted to pH 8.0 with 5N-KOH]. The suspension was introduced into a 2-liter aeration stirring tank, and the reaction was carried out at 37° C., 300 rpm and pH 8.0 for 10 hours. After the reaction, a supernatant was prepared from the reaction mixture by centrifugation (6000 rpm, 15 minutes, 4° C.) L-tryptophan in the supernatant was measured by liquid chromatography.

500 ml of the reaction mixture after the reaction was passed through a column of an ammonia-type strongly basic ion exchange resin ("Diaion SK-1B", a product of Mitsubishi Chemical Co., Ltd.) for the purification of L-tryptophan. The column was eluted, and the eluate was concentrated to precipitate crystals of L-tryptophan.

The results are shown in Table 21.

TABLE 21

| Strain | Concentration of the productd formed (g/liter) | Amount of the product purified (g/liter) |
|---|---|---|
| Strain harboring pCRY31tna (FERM BP-2717) | 8.0 | 3.0 |
| Strain harboring pCRY3KEtna | 8.8 | 3.2 |
| Strain harboring pCRY3KXtna | 9.0 | 3.5 |
| Strain harboring pCRY3tna | 0.06 | — |

We claim:

1. A plasmid vector which replicates and proliferates in Coryneform bacteria, which has been stabilized by the insertion of a DNA fragment which stabilizes the plasmid in Coryneform bacteria grown without genetic selection as compared to the stabilization under identical conditions of the plasmid without the DNA fragment, and which is obtained from plasmid pBY503 isolated from *Brevibacterium stationis* IFO 12144.

2. The plasmid vector according to claim 1, wherein the inserted DNA fragment has a size of about 7.4 kb and KpnI termini.

3. The plasmid vector according to claim 2, wherein the inserted DNA fragment, when digested with the restriction endonucleases indicated in Table 1 below, gives the recognition sites and sizes of the fragments indicated in Table 1:

TABLE 1

| Restriction endonuclease | Number of recognition sites | Size (kb) of fragments |
|---|---|---|
| Eco RI | 3 | 2.7, 2.5, 2.1, 0.1 |
| Xba I | 1 | 5.9, 1.5 |
| Sac I | 1 | 6.8, 0.6 |
| Sma I | 1 | 6.4, 1.0 |

4. The plasmid vector according to claim 1, wherein the inserted DNA fragment has a size of about 2.1 kb and KpnI and EcoRI termini.

5. The plasmid vector according to claim 4, wherein the inserted DNA fragment, when digested with the restriction endonucleases indicated in Table 2 below, gives the recognition sites and sizes of the fragments indicated in Table 2:

TABLE 2

| Restriction endonuclease | Number of recognition sites | Size (kb) of fragments |
|---|---|---|
| Sac I | 1 | 1.4, 0.7 |
| Xba I | 1 | 1.5, 0.6 |
| Hind III | 1 | 1.6, 0.5 |
| Kpn I | 0 | 2.1 |

6. The plasmid vector according to claim 1, wherein the inserted DNA fragment contains the following nucleotide sequence:

```
        10          20          30          40          50          60
GGTACCCGTA  TTTATGGTTA  AGGAGTGAGA  ATGATTCTAG  GAATCGTTAA  CATTAAGGC
        70          80          90         100         110         120
GGGGTGGGAA  AAACAACGAC  GGCAATCTTA  TCTCGGTAGC  GCTCTTGCTG  CTGAAGGTAA
       130         140         150         160         170         180
AAAGGTCACG  CTGATAGATC  TTGACCGTCA  AGGCACTGCG  ATGGATTGGG  CGGAATCCGC
       190         200         210         220         230         240
TGAAGAAGCT  GGCACGCCAT  TGGACTTTGA  AGTCTCGATA  GCTATTCCTC  GACAGCTCGA
       250         260         270         280         290         300
GCGCATTACC  TCCTTGCTAC  CTGATGATGA  GGTAGTCATC  ATTGATACAC  CGCCTGGAGA
       310         320         330         340         350         360
CGAACCAATC  TATCAACGCC  ACGTTGCAGG  TATCGGATTT  CATTATCATC  CCTGCCGCCC
       370         380         390         400         410         420
CGCAGCGCGA  ATGTGGCGCA  GATGTGGAAA  GTTATCGACG  TTCTTGAGCA  AACCCCTTAT
       430         440         450         460         470         480
GCTGCTTTGC  TTACTCAAGT  GCGTGCTGGA  ACGACCGCAA  TATCGGAAGC  AGTCGATGCG
       490         500         510         520         530         540
CTTAAAGAGG  CGGATGTGAG  TTTCTTTGAA  ACGTTATTCC  TTGCCAGAGG  CTTTTCACCG
       550         560         570         580         590         600
CAGTTTCAGG  ACTAAACCAA  CTGATTTAGG  TGAGTACACC  CAGGTTCTCG  CCGAGATAAA
       610         620         630         640         650         660
GGAGTCGTTT  TAATGGCCGT  TCAAAAGACC  AATTCTATGA  AGCGCCAGCC  TAAATCCACC
       670         680         690         700         710         720
GCACGAGAGT  CAGCGGATAT  TCGAAAGCCT  TTGCCTCACG  CAATCAAAGC  GATCATACTG
       730         740         750         760         770         780
TCAAGCTCAC  CGTGGAGCTT  GATTCACGTC  TTCACCGTTG  AGCTCACAAG  TGCCGCAGCT
       790         800         810         820         830         840
TTGCAGTCTG  TGACCATGCG  AGAGATTATT  CACGACGCCG  TAGAAGCAGA  GCTAAAAAAG
       850         860         870         880         890         900
CATAAGAACT  AGCTGCTGTA  TTTACGGGTA  CTGTATTTAC  AGCTATACAG  TTCCCCGTTC
       910         920         930         940         950         960
ATTGGCGTTA  TTTCACCCGC  CGCGAGCATC  GTTTACTGAA  TTAGCTCAGA  GGCCAACGCT
       970         980         990        1000        1010        1020
TCATAATCTG  GCATATCATC  GGGAATACGG  CAGCACTGAG  CATCCTCGCT  ATAACCTATG
```

-continued

| 1030 | 1040 | 1050 | 1060 | 1070 | 1080 |
|---|---|---|---|---|---|
| GCAGCGCTCT | TGCGGGTCGC | TTTAACGCCT | ACCTTGTTCA | ACATTTCTTG | ATACATAGGT |
| 1090 | 1100 | 1110 | 1120 | 1130 | 1140 |
| TCATCCGTTC | TCGGCCACAG | CCAAACATGA | TGGTCGGCGC | ATTGATAGCC | AAAAGGGTTC |
| 1150 | 1160 | 1170 | 1180 | 1190 | 1200 |
| GACGTGTTGG | TTCAACAGAC | ATCGACGAGC | CATCGAAGGG | TACTACACAG | TCGACGATGA |
| 1210 | 1220 | 1230 | 1240 | 1250 | 1260 |
| CGACTGCATC | ATCGCCAAGA | GATACCTCAA | GCTGTTGAAT | ATTGGCGCGA | AGTCGTGCCA |
| 1270 | 1280 | 1290 | 1300 | 1310 | 1320 |
| AGCTCAGCTA | TCTCATGAGC | TTGTAGCATT | GCATCAATCG | GAAACTCGTG | AACCTCAATG |
| 1330 | 1340 | 1350 | 1360 | 1370 | 1380 |
| GGGCTGACAT | TGCCGTTTTG | ATGTGCAAGC | TTGAGCCAGT | GTGCTGCCCC | TCCGTCCATG |
| 1390 | 1400 | 1410 | 1420 | 1430 | 1440 |
| AGGTGTCTGC | GATGCGAGCT | TTTTTGCCCC | TCCGGCTATA | CGCTTCTGCC | AATAGCGCGG |
| 1450 | 1460 | 1470 | 1480 | 1490 | 1500 |
| CGTTGGTGCT | GCGCATGAGG | CCGCCTTTAA | GGTTTGCTAC | TGAGATAATC | ATGTCTGCCT |
| 1510 | 1520 | 1530 | 1540 | 1550 | 1560 |
| TCCCGTGCGT | TGTGGATTCC | CCAAAATGAT | ACTTATAGTC | TGTCGACCTA | AGGGTTCACC |
| 1570 | 1580 | 1590 | 1600 | 1610 | 1620 |
| GCTCGATTCT | GGATAGGTGG | TTGAAGATCA | GCGCCTATTG | CAGGAAGTAG | GCAACGAGTC |
| 1630 | 1640 | 1650 | 1660 | 1670 | 1680 |
| CGGTCTGCAC | GTAAAGAAAA | GGGATTGTCG | CAAGAAAGTC | TTGCTCATCT | TTCAGGACTG |
| 1690 | 1700 | 1710 | 1720 | 1730 | 1740 |
| CACCGACATA | CGTCAGCTCG | ATTGAGCGCG | GGGAGCGGAA | TCTCTCAGTG | CTTAATTTGC |
| 1750 | 1760 | | | | |
| TTACCCTGGC | AACTAGTTCT | AGA | | | |

7. The plasmid vector of claim 1, wherein the plasmid vector is selected from the group consisting of pCRY21, pCRY2KE, pCRY2KX, pCRY31, pCRY3KE or pCRY3KX.

8. A recombinant plasmid composed of the plasmid vector of claim 7, into which a DNA fragment at least containing a tryptophan synthase gene and a DNA fragment containing a promotor and an operator for controlling the expression of said gene are introduced.

9. A recombinant plasmid of claim 8, wherein the recombinant plasmid is selected from the group consisting of pCRY31trpl, pCRY3KEtrpl or pCRY3KXtrpl.

10. A recombinant plasmid composed of the plasmid vector of claim 7, into which a DNA fragment at least containing a tryptophanase gene and a DNA fragment containing a promotor and an operator for controlling the expression of said gene are introduced.

11. The recombinant plasmid of claim 10, wherein the recombinant plasmid is selected from the group consisting of pCRY31tna, pCRY3KEtna or pCRY3KXtna.

* * * * *